(12) United States Patent
Nolan

(10) Patent No.: US 11,621,067 B1
(45) Date of Patent: Apr. 4, 2023

(54) METHOD FOR GENERATING PERSONALIZED RESISTANCE TRAINING PROGRAM

(71) Applicant: Nicole Nolan, Santa Clarita, CA (US)

(72) Inventor: Nicole Nolan, Santa Clarita, CA (US)

(*) Notice: Subject to any disclaimer, the term of this patent is extended or adjusted under 35 U.S.C. 154(b) by 328 days.

(21) Appl. No.: 16/911,191

(22) Filed: Jun. 24, 2020

(51) Int. Cl.
| | |
|---|---|
| G16H 20/30 | (2018.01) |
| G09B 19/00 | (2006.01) |
| A63B 24/00 | (2006.01) |
| G06N 20/00 | (2019.01) |
| A63B 23/04 | (2006.01) |
| A63B 23/12 | (2006.01) |

(52) U.S. Cl.
CPC ........... *G16H 20/30* (2018.01); *G09B 19/003* (2013.01); *A63B 23/1209* (2013.01); *A63B 24/0003* (2013.01); *A63B 24/0062* (2013.01); *A63B 24/0075* (2013.01); *A63B 2023/0411* (2013.01); *G06N 20/00* (2019.01)

(58) Field of Classification Search
None
See application file for complete search history.

(56) References Cited

U.S. PATENT DOCUMENTS

| | | | |
|---|---|---|---|
| 11,065,506 B2* | 7/2021 | Lin | A63B 21/078 |
| 11,207,556 B2* | 12/2021 | Silveira | A63B 21/0626 |
| 2019/0046107 A1* | 2/2019 | Jang | A61B 5/4519 |
| 2019/0344121 A1* | 11/2019 | Wells | A61B 5/1118 |

* cited by examiner

*Primary Examiner* — Ronald Laneau
(74) *Attorney, Agent, or Firm* — Leavitt Eldredge Law Firm

(57) ABSTRACT

A computer-implemented method of creating a personalized weight training program for users in a one-on-one fitness setting and/or group fitness setting. The method includes the input of user information by the user, input of user information by a machine learning model, or a combination thereof to create the personalized weight training program. The method includes strength and weakness assessment of the muscles of a user and progress assessment of the user and/or between users.

2 Claims, 2 Drawing Sheets

US 11,621,067 B1

METHOD FOR GENERATING PERSONALIZED RESISTANCE TRAINING PROGRAM

BACKGROUND

1. Field of the Invention

The present invention relates generally to exercise systems, and more specifically to an weight training program system that generates one or more personalized resistance training programs for users in a one-on-one setting and/or group fitness setting.

2. Description of Related Art

Weight training program systems are well known in the art and are effective means to guide users during exercise. Commonly in the art, users hire a personal trainer to help educate and assist them with selecting the types of workouts to meet their desired fitness goals. One of the problems commonly associated with this is limited efficiency. For example, many conventional weight training program systems are not personalized to an individual user and are often targeted to generalized groups.

Accordingly, although great strides have been made in the area of weight training program systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
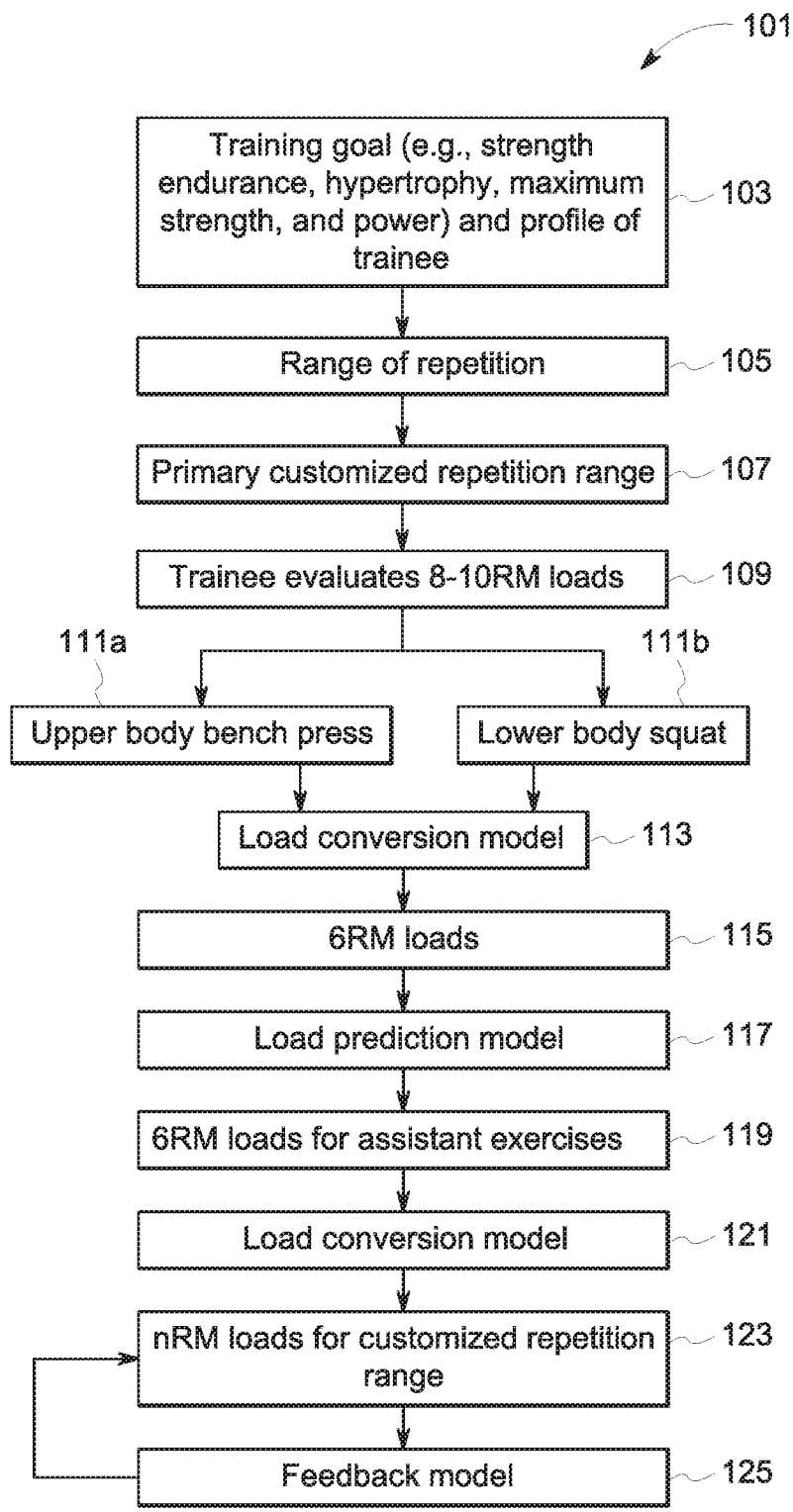
FIG. 1 is a flow diagram of a preferred embodiment of a computer-implemented personalized resistance training program system, illustrating a method to create a personalized resistance training program based on input of information.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional weight training systems. Specifically, the system of the present invention evaluates the strength and weakness of a user with respect to individual sizes. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Reference to "machine learning model" means a system that analyzes data and establishes models to make predictions and decisions without the system being explicitly programmed to do so.

Reference to "resistance training" means a form of exercise that improves muscular strength and endurance.

Reference to "RM" means repetition maximum.

Reference to "trainee" means a user taking part in the computer-implemented personalized resistance training program system.

Reference to "trainer" means an individual overseeing the computer-implemented personalized resistance training program system. The functions of a trainer include, but are not limited to, motivate the trainee, assess the progress of the trainee, and modify the resistance training program of the trainee if needed.

Reference to "n" represents a whole number value of the repetition maximum.

Referring now to the drawings wherein like reference characters identify corresponding or similar elements throughout the several views, FIG. 1 depicts a flow diagram of a computer-implemented personalized resistance training program system illustrating a method to create a personalized resistance training program in accordance with a preferred embodiment of the present application. It will be appreciated that system 101 overcomes one or more of the above-listed problems commonly associated with conventional weight training program systems. It will be further appreciated that additional steps are also contemplated in the preferred and alternative embodiments.

Figure 3:
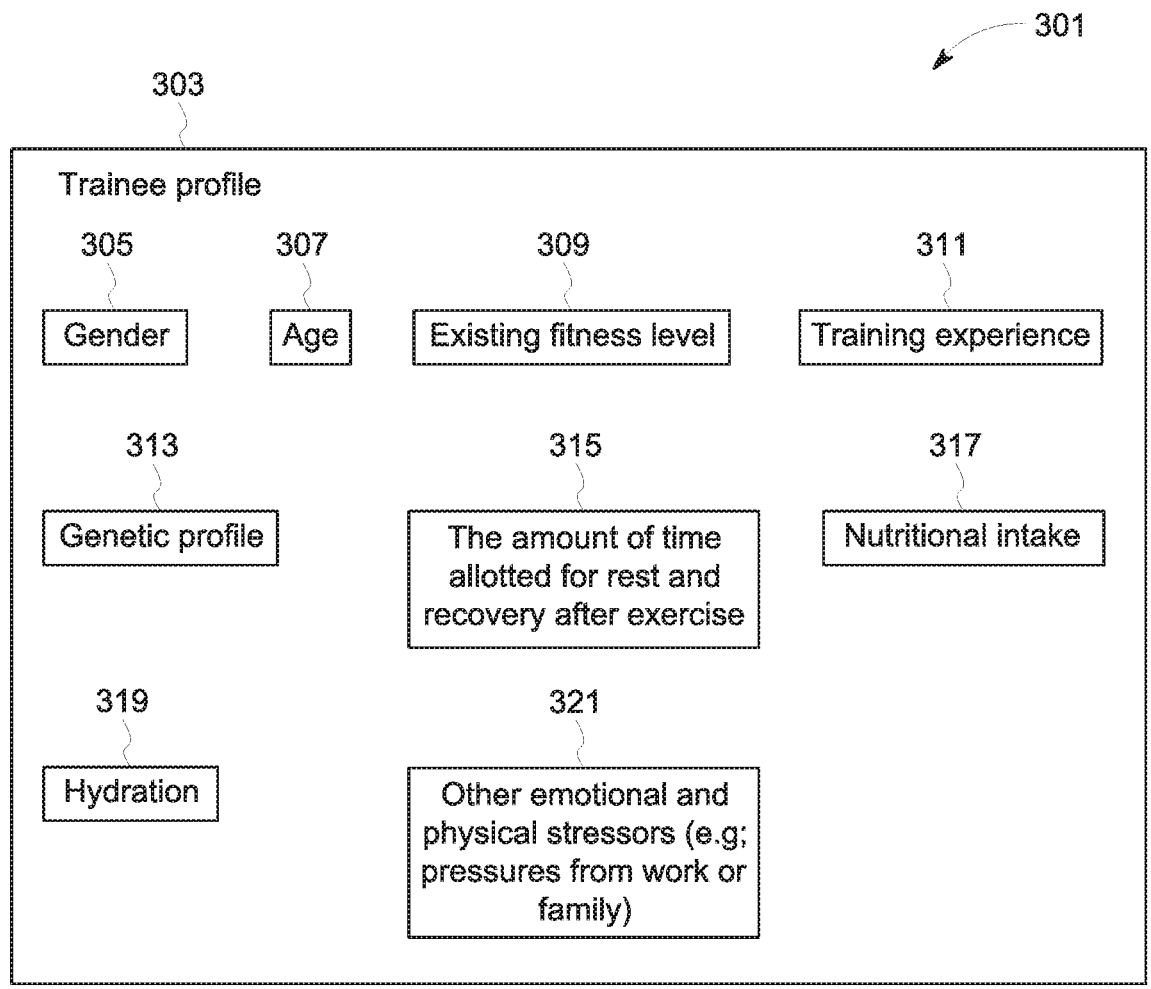
FIG. 3 is a schematic of a trainee profile in accordance with the present application.

In the contemplated embodiment, the method 101 initiates with step 103 of selecting a training goal and inputting the profile of a trainee (see FIG. 3 for trainee profile). The types of training goals include, but are not limited to, strength endurance, hypertrophy, maximum strength and power. The method 101 also includes step 105 of displaying a range of repetition used specifically for the type of training goal that is selected from step 103.

The method 101 also includes a step 107 of the generation of a primary customized repetition range for the selected training goal. It is contemplated and will be appreciated that a machine learning model may be used to generate the primary customized repetition range.

The method 101 also includes step 109 of the trainee evaluating the primary customized repetition range (e.g., 8-10RM loads) for a major exercise for both the upper body step 111a (e.g., bench press) and lower body step 111b (e.g., squat). The method 101 then includes step 113 of applying the load conversion model to convert the load that the trainee evaluates in step 109 into nRM loads (e.g., 6RM loads as shown in step 115). The method 101 also includes step 117 of applying the load prediction model to infer nRM loads (e.g., 6RM loads as shown in step 119) for assistant exercises for both the upper body and lower body from the nRM loads (e.g., 6RM loads as shown in step 119) of bench press and squat, respectively. The method then includes step 121 of applying the load conversion model to convert the nRM loads (e.g., 6RM loads as shown in steps 115, 119) to nRM loads required by the customized repetition range.

Furthermore, the method 101 includes step 125 of applying the feedback model which incorporates the feedback from the trainee into the customized repetition range in step 123. It is contemplated and will be appreciated that the feedback model can also detect the strength and weakness of the trainee and thus adjusts the nRM loads for customized repetition range automatically. It is further contemplated and will be appreciated that other machine learning models may be utilized to detect the strength and weakness of the trainee.

It is contemplated and will be appreciated that the load conversion model in step 113 converts loads between different nRM (e.g., from 10RM to 6RM). The load conversion model also allows conversion for higher nRM. For example, for a high nRM such as 16RM, 18RM, etc., a linear regression model is used to infer the percentage of the higher nRM with respect to 1RM, which is shown in the following equation:

$$nRM\ percentage = LR(1\text{-}RM\ percentage, 2\text{-}RM\ percentage, \ldots, (n\text{-}1)RM\ percentage)$$

where nRM percentage is the percentage of the nRM with respect to 1 RM and the model takes all the proceeding RM percentages as input, LR( ) is the linear regression model.

It is also contemplated and will be appreciated that the load prediction model in step 117 predicts the loads of assistant exercises from the load of major exercise. For example, the load prediction model applies linear regression to obtain the equations between the 6RM loads of major exercises and 6RM loads of assistant exercises.

It is further contemplated and will be appreciated that method 101 can incorporate a plurality of linear regression models continuously to generate customized repetition ranges. For example, method 101 evaluates the strength and weakness of a trainee with respect to individual exercises by using the estimated loads and repetitions as baselines. If the trainee can do more repetitions than the estimated baseline, the exercise represents the strength of the trainee. In contrast, if the trainee can do fewer repetitions than the estimated baseline, the exercise represents the weakness of the trainee. Method 101 automatically adjusts the training program to improve the weakness of the trainee via the plurality of linear regression models based on the last RM.

It is further contemplated and will be appreciated that method 101 can be implemented in a one-on-one fitness setting between the trainer and trainee, in a group fitness setting between the trainer and one or more trainees, or a combination thereof.

It should also be appreciated that one of the unique features believed characteristic of the present application is that it generates a personalized training program with high accuracy and efficiency and requires the evaluation of only two major exercises rather than on all exercises. Furthermore, the personalized training program tracks the progress of strengths and weaknesses of the muscle groups of the trainee as well as comparing the progress of the trainee to other trainees.

Figure 2:
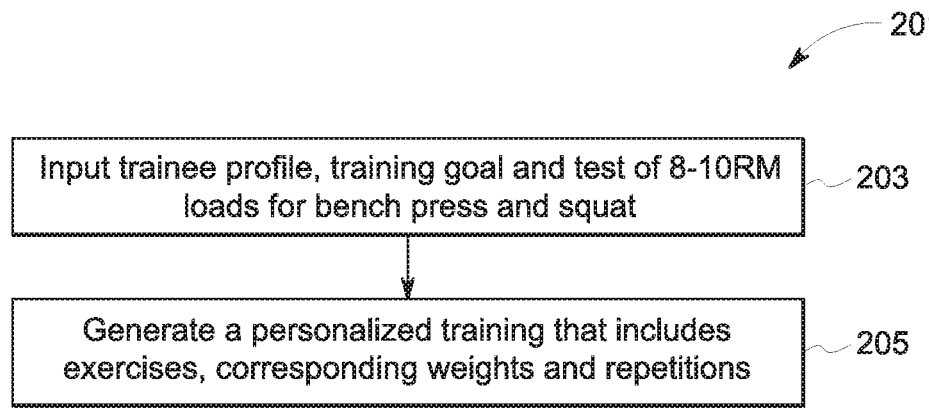
FIG. 2 is a flow diagram of the method of use of an embodiment of a personalized resistance training program in accordance with the present application.

FIG. 2 depicts a flow diagram of a method of use associated with system 101. The method 201 initiates with step 203 of inputting trainee profile, training goal and test of 8-10RM loads for bench press and squat. The method then includes step 205 of generating a personalized training that includes exercises, corresponding weights and repetitions.

FIG. 3 presents a schematic 301 of a trainee's profile in accordance with the present application. The trainee profile 303 includes, but is not limited to, gender 305, age 307, existing fitness level 309, training experience 311, genetic profile 313, amount of time allotted for rest and recovery after exercise 315, nutritional intake 317, hydration 319, and other emotional and physical stressors (e.g., pressures from work or family) 321. The trainee's profile 303 incorporates into step 103 of FIG. 1.

As described herein, computer software products can be written in any of various suitable programming languages, such as C, C++, C#, Pascal, Fortran, Perl, Matlab (from MathWorks), SAS, SPSS, JavaScript, AJAX, Java, Swift and Objective C. The computer software product can be an independent application with data input and data display modules. Alternatively, the computer software products can be classes that can be instantiated as distributed objects. The computer software products can also be component software (e.g., Java Beans or Enterprise Java Beans). Much functionality described herein can be implemented in computer software, computer hardware, or a combination thereof.

Furthermore, a computer that is running the previously mentioned computer software can be connected to a network and can interface to other computers using the network. The network can be an intranet, internet, or the Internet, among others. The network can be a wired network (e.g., using copper), telephone network, packet network, an optical network (e.g., using optical fiber), or a wireless network, or a combination of such networks. For example, data and other information can be passed between the computer and components (or steps) of a system using a wireless network based on a protocol, for example Wi-Fi (IEEE standard 802.11 including its sub standards a, b, e, g, h, i, n, et al.). In one example, signals from the computer can be transferred, at least in part, wirelessly to components or other computers.

It is to be understood that although various components are illustrated herein as separate entities, each illustrated component represents a collection of functionalities which can be implemented as software, hardware, firmware or any combination of these. Where a component is implemented as software, it can be implemented as a standalone program, but can also be implemented in other ways, for example as part of a larger program, as a plurality of separate programs, as a kernel loadable module, as one or more device drivers or as one or more statically or dynamically linked libraries.

As will be understood by those familiar with the art, the invention may be embodied in other specific forms without departing from the spirit or essential characteristics thereof. Likewise, the particular naming and division of the portions, modules, agents, managers, components, functions, procedures, actions, layers, features, attributes, methodologies and other aspects are not mandatory or significant, and the mechanisms that implement the invention or its features may have different names, divisions and/or formats.

Furthermore, as will be apparent to one of ordinary skill in the relevant art, the portions, modules, agents, managers, components, functions, procedures, actions, layers, features, attributes, methodologies and other aspects of the invention can be implemented as software, hardware, firmware or any combination of the three. Of course, wherever a component of the present invention is implemented as software, the component can be implemented as a script, as a standalone program, as part of a larger program, as a plurality of separate scripts and/or programs, as a statically or dynamically linked library, as a kernel loadable module, as a device driver, and/or in every and any other way known now or in the future to those of skill in the art of computer programming. Additionally, the present invention is in no way limited to implementation in any specific programming language, or for any specific operating system or environment.

Furthermore, it will be readily apparent to those of ordinary skill in the relevant art that where the present invention is implemented in whole or in part in software, the software components thereof can be stored on computer readable media as computer program products. Any form of computer readable medium can be used in this context, such as magnetic or optical storage media. Additionally, software portions of the present invention can be instantiated (e.g., as object code or executable images) within the memory of any programmable computing device.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A computer-implemented method to generate one or more personalized resistance training programs, the computer-implemented method comprising:
   providing a computer having an algorithm and a database;
   allowing a user to select a training goal and inputting his or her training profile via the computer;
   generating one or more personalized resistance training programs via the algorithm based on user information inputted by the user, user information inputted by a machine learning model, or a combination thereof;
   allowing a user to modify the personalized resistance training programs;
   tracking the progress of the strengths and weaknesses of the muscle groups of a user via user input;
   comparing the strengths and weaknesses of the muscle groups of a user with one or more other users via information found in the database;
   wherein the machine learning model utilizes a load conversion model, a load prediction model, and a feedback model to generate one or more personalized resistance training programs.

2. The method of claim 1 wherein the training profile includes gender, age, existing fitness level, training experience, genetic profile, the amount of time allotted for rest and recovery after exercise, nutritional intake, hydration, and other emotional and physical stressors.

* * * * *

UNITED STATES PATENT AND TRADEMARK OFFICE
CERTIFICATE OF CORRECTION

Page 1 of 1

PATENT NO. : 11,621,067 B1
APPLICATION NO. : 16/911191
DATED : April 4, 2023
INVENTOR(S) : Nicole K. Nolan and Lawrence R. Nolan It is certified that error appears in the above-identified patent and that said Letters Patent is hereby corrected as shown below:

On the Title Page

Item (12) should read:
Nolan et al.

Item (72) list both inventors as:
Nicole K. Nolan of Santa Clarita, CA
Lawrence R. Nolan of Santa Clarita, CA Signed and Sealed this
Eleventh Day of February, 2025

Coke Morgan Stewart
*Acting Director of the United States Patent and Trademark Office*